(12) United States Patent
Vaze et al.

(10) Patent No.: US 10,846,774 B2
(45) Date of Patent: Nov. 24, 2020

(54) SYSTEM AND METHOD FOR PATIENT SPECIFIC CUSTOMIZED RECOMMENDATIONS OF HOSPITALS AND ACOS

(71) Applicant: KONINKLIJKE PHILIPS N.V., Eindhoven (NL)

(72) Inventors: Vikrant Suhas Vaze, White Plains, NY (US); Saeed Reza Bagheri, Croton on Hudson, NY (US); Hanqing Cao, Mahwah, NJ (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 570 days.

(21) Appl. No.: 14/339,533

(22) Filed: Jul. 24, 2014

(65) Prior Publication Data
US 2015/0032466 A1    Jan. 29, 2015

Related U.S. Application Data

(60) Provisional application No. 61/857,804, filed on Jul. 24, 2013.

(51) Int. Cl.
*G06Q 30/06* (2012.01)
*G06Q 50/22* (2018.01)

(52) U.S. Cl.
CPC ......... *G06Q 30/0631* (2013.01); *G06Q 50/22* (2013.01)

(58) Field of Classification Search
CPC ............ G06Q 30/0631; G06Q 50/22; G06Q 30/0269; G06Q 50/24

USPC ............................................................ 705/2
See application file for complete search history.

(56) References Cited

U.S. PATENT DOCUMENTS

| | | | | |
|---|---|---|---|---|
| 5,778,345 | A * | 7/1998 | McCartney | G06Q 10/06 705/2 |
| 5,924,073 | A * | 7/1999 | Tyuluman | G06F 19/328 705/2 |
| 8,494,881 | B1 | 7/2013 | Wizig | |
| 2006/0015369 | A1 | 1/2006 | Bachus et al. | |
| 2006/0026037 | A1* | 2/2006 | Lubbert | G06Q 10/10 705/2 |

(Continued)

OTHER PUBLICATIONS

Boyce, T. et al "Choosing a high Quality Hospital. The role of nudges, scorecard design and information". The King's Fund, 2010.

(Continued)

*Primary Examiner* — Hiep V Nguyen

(57) ABSTRACT

A system, method and computer readable storage medium for selecting a medical provider from a plurality of available medical providers. The selection being made by receiving medical data and one of geographical and financial data corresponding to a patient, comparing the medical data and the one of the geographical and financial data corresponding to the patient to corresponding data of a plurality of medical provider databases to determine a relationship therebetween and generating, via a recommendation generator, a recommendation of a first medical provider for the patient based on the medical data and the one of geographical and financial data and the comparison to the corresponding data of the medical provider databases.

19 Claims, 3 Drawing Sheets

(56) References Cited

U.S. PATENT DOCUMENTS

| | | | | |
|---|---|---|---|---|
| 2006/0094949 | A1* | 5/2006 | Coonce | A61B 5/0002 600/407 |
| 2008/0033751 | A1* | 2/2008 | Greene | G06F 19/328 705/2 |
| 2010/0145723 | A1 | 6/2010 | Hudson et al. | |
| 2010/0235295 | A1 | 9/2010 | Zides et al. | |
| 2010/0312798 | A1* | 12/2010 | Dutta | G06F 19/3443 707/780 |
| 2011/0119084 | A1 | 5/2011 | Brandt | |
| 2012/0035948 | A1* | 2/2012 | Borton | G06Q 50/22 705/2 |
| 2012/0078648 | A1* | 3/2012 | Reiner | G06F 19/00 705/2 |

OTHER PUBLICATIONS

MHA Keystone Center for Patients Selecting a Hospital. http://www.mhakeystonecenter.org/select.htm. (2013).

Lako, C.J. et al. "Demand-Driven Care and Hospital Choice. Dutch Health Policy Toward Demand-Driven Care: Results from a Survey into Hospital Choice". Health Care Anal (2009) 17:20-35.

Fisher, E.S. et al. "Accountable Care Organizations". The Journal of the American Medical Association. Oct. 20, 2010, vol. 304, No. 15.

Berwick, D.M. "ACOs—Promise, Not Panacea". The Journal of the American Medical Association. Sep. 12, 2012, vol. 308, No. 10.

* cited by examiner

SYSTEM AND METHOD FOR PATIENT SPECIFIC CUSTOMIZED RECOMMENDATIONS OF HOSPITALS AND ACOS

BACKGROUND

The selection of a medical care professional or facility for treatment is an important one, affecting a level, quality and total cost of care received. Studies indicate that patients typically rely on simplistic measures when making this selection, relying solely on, for example, their physician's opinion, proximity to a care facility and the general reputation of the facility. By failing to account for a match between the facility's expertise in caring for a patient's specific medical history, patients are prevented from selecting the best and most cost-effective facility for their particular needs. Additionally, with the increased importance of Accountable Care Organizations (ACOs) through new payment models and government mandates, the patient's choice of ACOs, hospital and hospital network has become even more complex. This is because the selection process now needs to consider the entire bundle of expertise offered by all members of the ACO or hospital network and how well they match with not just past and present medical conditions of the patient but also their planned and likely health-related conditions. These complex dynamics require a fresh perspective to hospital selection decisions that not only equip the patients with better systems and tools to make the right choice but also create easy mechanisms for the hospitals, hospital networks, ACOs and insurance providers to guide these decisions in the direction most favorable to them.

SUMMARY

A system, method and computer readable storage medium for selecting a medical provider from a plurality of available medical providers. The selection being made by receiving medical data and one of geographical and financial data corresponding to a patient, comparing the medical data and the one of the geographical and financial data corresponding to the patient to corresponding data of a plurality of medical provider databases to determine a relationship therebetween and generating, via a recommendation generator, a recommendation of a first medical provider for the patient based on the medical data and the one of geographical and financial data and the comparison to the corresponding data of the medical provider databases.

BRIEF DESCRIPTION OF THE DRAWINGS

Several embodiments of the invention will be described in the following by way of example and with reference to the accompanying drawings in which.

DETAILED DESCRIPTION

The exemplary embodiments may be further understood with reference to the following description and appended drawings. The exemplary embodiments propose a system and method for the customized selection of a hospital, hospital network and ACO for both emergency and non-emergency situations. In a first exemplary embodiment, the system generates a patient-accessible database of current information of the patient, as will be described in greater detail later on. The system may further include a database of historical medical data of the patient. The system may further include an insurance provider-accessible database and an optional accompanying incentive generation process, a hospital-accessible database and an optional accompanying incentive generation process, a hospital network-accessible database and an optional accompanying incentive generation process and an ACO-accessible database and an optional accompanying incentive generation process. The system may further include a computerized process to generate optimal recommendations for the patient based on any single or combination of the above-recited databases. The exemplary system employs an algorithm configured to match current patient data with that of previous patients exhibiting similar symptoms, having similar medical conditions or otherwise meeting the criteria of being "similar" to the current patient, as will be defined and described in greater detail later on. The system uses this data along with user-submitted preferences of location, cost, etc. and insurance-provider incentives (if applicable), hospital incentives (if applicable), hospital-network incentives (if applicable) and ACO incentives (if applicable) to provide a recommendation to the current patient of one or more optimal hospitals, hospital networks or ACOs. The system may further comprise a terminal (e.g., user interface, display, etc.) to permit interaction of the patient with the exemplary recommendation generation tool during one or both of an emergency and a non-emergency situation.

Figure 1:
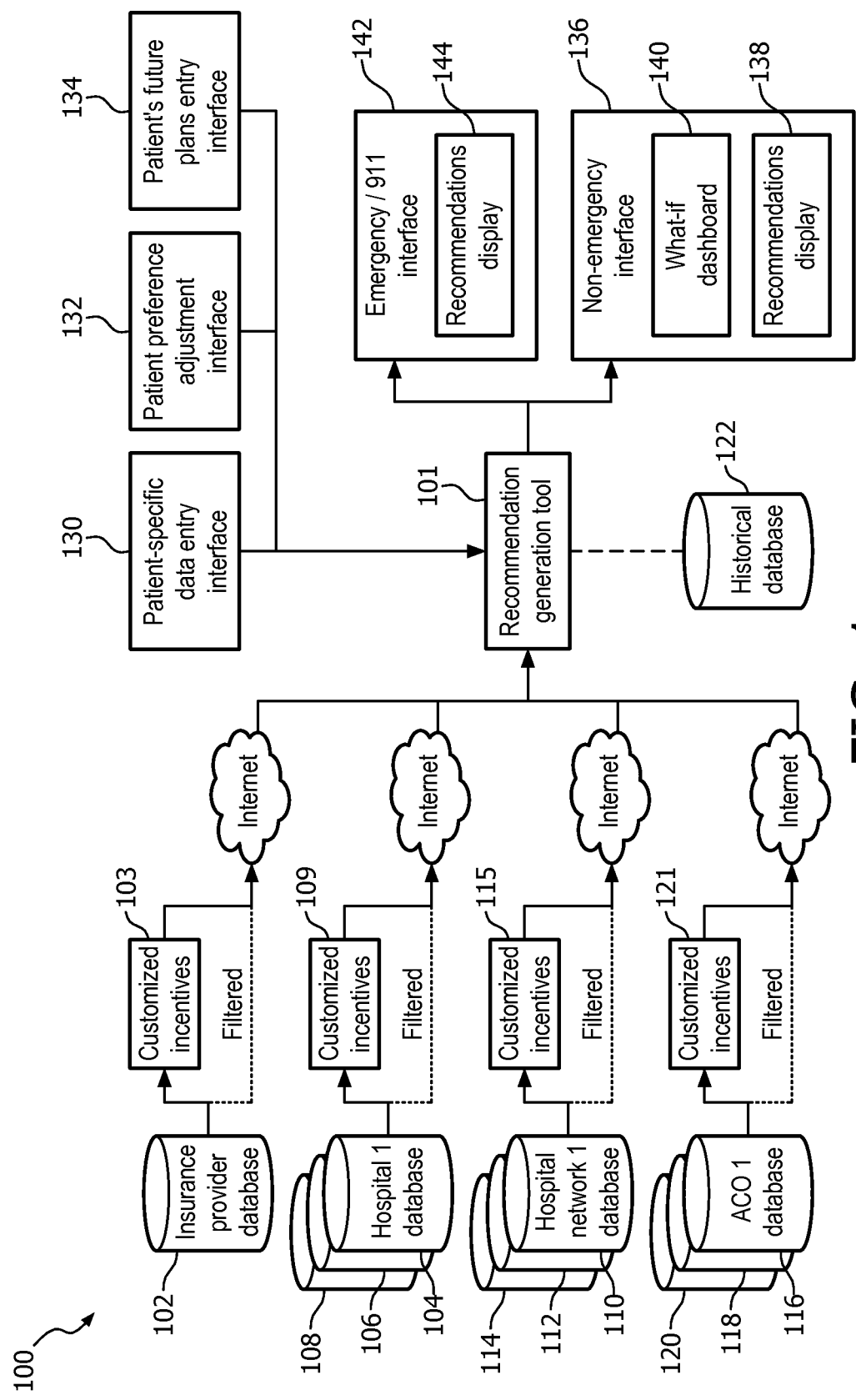
FIG. 1 depicts a schematic drawing of a system according to an exemplary embodiment.
Figure 2:
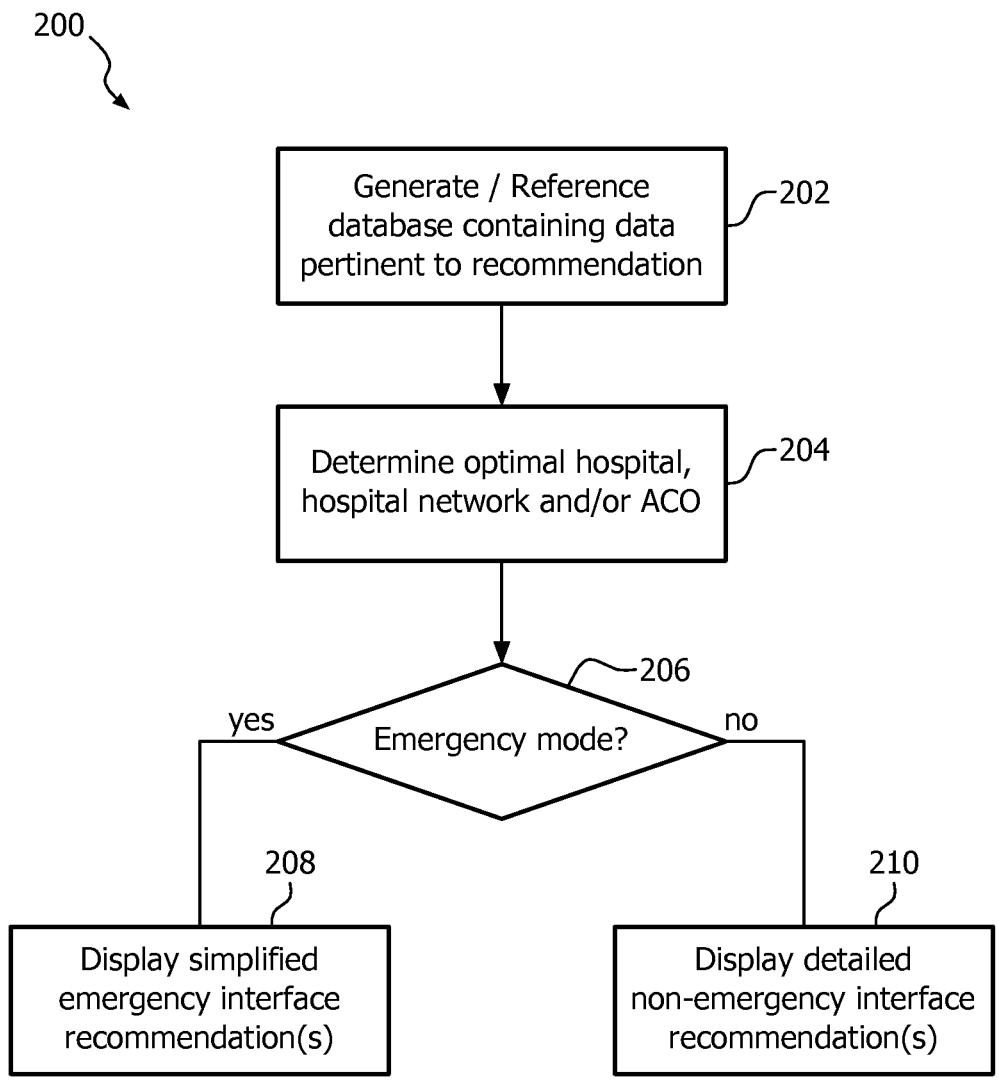
FIG. 2 depicts a flow diagram of an exemplary method.

An exemplary embodiment is described in greater detail with respect to FIGS. 1-2, which depict an exemplary system 100 and method 200. In a first exemplary step 202, a plurality of reference databases are generated. Alternatively, the system 100 references any plurality of previously generated databases as opposed to generating new reference databases. As shown in FIG. 1, an insurance provider database 102 is provided and includes information proprietary to that insurance provider on demographic, medical, claims-related and financial aspects of the individuals served in the past and present by the insurance provider as well as information publicly reported by that insurance provider. Optionally, the insurance provider database 102 includes this data for a particular subset of the individuals served by the insurance provider. For example, the subset may be optionally filtered to include only data relating to patients that match one or more medical history criteria of the current patient. As those skilled in the art will understand, this filtering may be manually prompted by the patient or may be automatically performed by the system 100. A filtered version of the insurance provider database 102 is made available to an exemplary recommendation generation tool 101, with a further filtered version being made available to the patient or other end-user.

The system 100 further includes an insurance provider incentive process 103 connected to the insurance provider database 102 and adapted to permit the system 100 to transmit incentives customized to the individual patient's case to the recommendation generation tool 101 and influence the patient's selection. The insurance provider database 102 and the incentive process 103 are provided to the recommendation generation tool 101 over, for example, an internet connection or any other type of network. The insurance provider can provide incentives via a list provided in the incentive process 103 to potentially change patients marginally disposed to choose between first and second hospitals by providing additional incentives for the patient to select, for example, the second hospital. For example, the incentive process 103 may include data with respect to hospitals affiliated with the insurance provider and give preference to such in-network hospitals, hospital networks or ACOs. The incentive process 103 may include incentives including, but not limited to, monetary incentives, priority-based incentives, etc. This may be done to, for example, minimize the overall reimbursement required to be paid by the insurance provider to the selected hospital and may be achieved by, for example, providing a lower deductible and/or lower co-payment rate for the second hospital than for the first hospital. The insurance provider can use patient data from previous patients having similar medical credentials to model the patient choice. An exemplary algorithm used to determine a patient's similarity to previous patients will be described in greater detail later on. It is noted that although the system and method is disclosed with respect to a single insurance provider database 102, any number of insurance provider databases may be employed without deviating from the scope of the disclosure.

The system 100 also includes first, second and third hospital databases 104, 106, 108, each of which includes information proprietary to that hospital on procedural, diagnostic, outcomes-related and financial aspects of the patients served in the past and present by the hospital as well as the information publicly reported by that hospital. A filtered version of each of the first, second and third databases 104, 106, 108 is made available to the patient-specific recommendation generation tool 101 over the network. The first, second and third hospital databases 104, 106, 108 may further include a corresponding hospital incentive process 109 adapted to permit the hospitals to provide incentives tailored to specific patients to influence their choice. One particular criterion for deciding the incentive could be the proportion of empty beds and vacancies in the hospital. A hospital with many empty beds can decide to attract patients by providing special discounts, while a hospital which is running close to its capacity can decide to raise the charges to attract only those patients that can pay the premium rate, thus improving the hospital's bottom line. The incentive can include other criteria as well including, but not limited to, doctor/nurse availability, medical equipment availability, etc.

The system 100 also includes first, second and third hospital network databases 110, 112, 114, which are substantially similar to the first, second and third hospital database 104, 106, 108. The first, second and third hospital network databases 110, 112, 114 offer the additional possibility of directing patients to appropriate hospitals within one of the first, second and third hospital networks 110, 112, 114 to maximize a match between patient conditions/needs and hospital specific expertise, retain the patients within the first, second or third hospital network and to maximize the patient's satisfaction level. Additionally, availability of beds will also be one of the governing constraints in deciding the right incentive structure for each of the first, second and third hospital networks 110, 112, 114. A customized incentive process 115 may also be provided. When provided with a plurality of patients, the decision of the set of patients to be incentivized to come to a specific hospital within the hospital network can be made simultaneously. In one example, the following process may be used, wherein a set of hospitals $H_1$ through $H_n$ are provided under a network and a set of patients $Pt_1$ through $Pt_K$ are available. The revenue R to be generated from each patient (k) for each hospital (n) is $R_{n,k}$. Alternatively, the revenue measure can also be replaced by a combined measure with the aim of maximizing revenue, positive outcomes and patient satisfaction. The available number of vacancies in hospital n is $V_n$. The mathematical model for assigning a hospital from the hospital network is determined as follows:

$$\text{Maximize Revenue: } \sum_{n=1}^{N} \sum_{k=1}^{K} R_{n,k} \cdot y_{n,k}$$

$$\text{Subject to: } \sum_{n=1}^{N} y_{n,k} \leq 1 \, \forall \, k \in \{1, \ldots, K\}$$

$$\sum_{k=1}^{K} y_{n,k} \leq V_n \, \forall \, n \in \{1, \ldots, N\}$$

$$y_{n,k} \in \{0, 1\} \forall \, k \in \{1, \ldots, K\}, n \in \{1, \ldots, N\}$$

The system 100 also comprises first, second and third ACO databases 116, 118, 120 which include information proprietary to the hospitals within that ACO on procedural, diagnostic, outcomes-related and financial aspects of the patients served in the past and present by the ACO as well as the information publicly reported by the ACO. A filtered version of each of the first, second and third ACO databases 116, 118, 120 is made available to the patient-specific recommendation generation tool 101 over the network. Similar to the first, second and third hospital networks, the first, second and third ACOs can also make a decision of the set of patients to be incentivized via an incentive process 121 to come to a specific hospital within the ACO using models and methods disclosed above and described in greater detail below. Those skilled in the art will understand that the use of three hospitals, hospital networks and ACOs is only exemplary. The system 100 may include any number of these types of entities and, in some cases, may not include any of a particular type of entity (e.g., the system 100 may not include any hospital networks because there are no available hospital networks in the vicinity of the individual patient).

A historical database 122 including past medical data corresponding to the patient may be stored separately from the previously recited databases. The historical database 122 may be stored on the same server or cloud as the recommendation generation tool 101, or alternatively, the historical database 122 may be stored separately from the recommendation generation tool 101 and may be connected thereto via a network connection, as with the earlier recited databases. The historical database 122 contains results from previous uses of the recommendation generation tool 101 as well as the history of all the information entered by the patient, received over the network from the insurance provider, hospitals, hospital networks, ACOs etc. This can also include any information entered by the patients about their past experiences with specific healthcare/insurance providers. As those skilled in the art will understand, this data can be used to provide better modeling and optimization of the patient-specific recommendations.

Once the reference databases have been generated or properly referenced and linked to the recommendation generation tool 101 (e.g., via a network connection), the exemplary system 100 follows a predetermined algorithm to properly assign a hospital, hospital-network or ACO to the patient. In particular, $$h\left(\left(\overrightarrow{x_j(t)}, \overrightarrow{f_j(t)}, \overrightarrow{d_j(t)}\right)_{t \in T}\right)$$

is defined as the objective function $$h: \prod_{t=1}^{T} (S_x(t) \times S_f(t) \times S_d(t)) \to R$$

based on multiple criteria ($\vec{x}$, $\vec{f}$, $\vec{d}$), where $S_x(t)$, $S_f(t)$, $S_d(t)$ represent the $j^{th}$ hospital's performance data space, financial data space, and geographical data space at different time-periods t, respectively. Similarly, functions $$g_i(\vec{x_j}, \vec{f_j}, \vec{d_j})$$

where $g_i$: $S_x \times S_f \times S_d \to R$, describe constraint functions that each hospital, hospital network or ACO needs to meet in order to be considered by a specific patient. The resulting optimal recommendation generation problem is mathematically described below:

$$\left(\left(\overrightarrow{x_{j*}(t)}, \overrightarrow{f_{j*}(t)}, \overrightarrow{d_{j*}(t)}\right)_{t \in T}\right) = \mathrm{argmax}\, h\left(\left(\overrightarrow{x_j(t)}, \overrightarrow{f_j(t)}, \overrightarrow{d_j(t)}\right)_{t \in T}\right)$$

subject to: $g_i\left(\left(\overrightarrow{x_{j*}(t)}, \overrightarrow{f_{j*}(t)}, \overrightarrow{d_{j*}(t)}\right)_{t \in T}\right) \geq s_i, \forall\, i$ $j \in J$ Here $j^o$ is the recommended hospital/ACO and J is the set of all hospitals in the database. $s_i$ $\forall$i is the minimum level to meet the requirements specified by each of the constraints. The generated recommendation is optimized over a time horizon T that includes current and future time-periods.

The exemplary recommendation generation tool 101 disclosed herein may be used at any phase of medical diagnosis or treatment of the patient. Health-related, financial as well as geographical aspects of the suitability of a hospital from a specific patient's viewpoint evolve with time due to a number of reasons, including, but not restricted to, aging, plans to retire, plans to get pregnant, job change prospects, relocation plans, time-value-of-money, etc. The optimization formulation described by the above algorithm can take these expected/probable changes into account when optimizing the choice of hospitals/hospital networks/ACOs for a patient. Additionally, a patient could have some other secondary attributes in mind when selecting a healthcare facility. There is a possibility that such attributes are not accounted for in the recommendation generator tool 101 or it may be the case that there are some intangibles that the patient values. In such cases, it is useful to provide the patient with more than one "optimal" or "close to optimal" alternatives to choose from. This can be achieved by providing the patients with the second best, third best, etc. options, as deemed by the recommendation generation tool 101 rather than just a single most optimal recommendation. In this embodiment, the same above-disclosed algorithm is used but the first optimal recommendation is excluded from the choice set when selecting the second best option. The formulation above gets modified as follows: $j^n$ is the $n^{th}$-best option as obtained by the recommendation generator. The patient is then presented with a number of such options to choose from. The number of near-optimal options to be displayed can be a parameter that can be set through the patient-preference adjustment interface or may be a predetermined value (e.g., two options, three options, four options, etc). The exemplary algorithm for this embodiment is disclosed below:

$$\left(\left(\overrightarrow{x_{j^n}(t)}, \overrightarrow{f_{j^n}(t)}, \overrightarrow{d_{j^n}(t)}\right)_{t \in T}\right) = \mathrm{argmax}\, h\left(\left(\overrightarrow{x_j(t)}, \overrightarrow{f_j(t)}, \overrightarrow{d_j(t)}\right)_{t \in T}\right)$$

subject to: $g_i\left(\left(\overrightarrow{x_j(t)}, \overrightarrow{f_j(t)}, \overrightarrow{d_j(t)}\right)_{t \in T}\right) \geq s_i, \forall\, i$ $j \in J - \{j^1, j^2, \ldots, j^{n-1}\}$ The exemplary recommendation generation tool 101 may be used in both emergency and non-emergency situations and may be made available on a plurality of platforms. In a non-emergency situation, an algorithm is employed which aims to maximize a weighted sum of outcome-related benefits (x) and the negative of generalized travel costs (d) while ensuring that the financial costs are within budget (B) and a minimum percentage (P) of past outcomes were positive. The algorithm further accounts for the patient's age. In a specific example, a patient is provided who is currently covered under a private insurance plan through his/her employer. In the present embodiment, the patient will be 65 years old in two years and would be eligible for Medicare. Thus the calculation of financial costs needs to take into account the current financial costs under private insurance as well as future costs under Medicare. In particular, the algorithm is as follows:

maximize $[(w_x * x_1 - w_d * d_1)]$

Subject to: $f_1 + f_2 \leq B$ $\dfrac{x_2}{x_3} \geq P$ where $x_1$ represents the performance of the specific hospital/hospital network/ACO on similar patients in the past, $x_2$ represents the number of positive outcomes and $x_3$ represents the total number of outcomes of similar patients for that hospital/hospital network/ACO. $d_1$ is the net present value of the generalized travel cost from patient's home to hospital location which includes costs related to actual travel cost (e.g., gas charges, transit fares, etc.), cost of time lost in travel and cost of traveling efforts and treatment delays. The cost calculation may also account for the future plans of the patient. $f_1$ is the net present value of the total financial cost, over the next two years under the existing private insurance, of choosing a specific hospital/hospital network/ACO accounting for future plans of the patient and any incentives provided by the hospital/hospital network/ACO or the private insurance provider. $f_2$ is the net present value of the total expected financial costs, after two years onward under Medicare, of choosing a specific hospital/hospital network/ACO accounting for future plans of the patient and accounting for any incentives provided by the hospital/hospital network/ACO or the public insurance provider. $w_x$ and $w_d$ are weight parameters, B is the budget parameter and P is the parameter describing the minimum percentage of positive past outcomes. These preference-related parameters can be adjusted by the patient. They can also be different for emergency and non-emergency situations. (e.g., the relative importance of travel distance will be significantly greater for emergency situations).

The patient can enter a number of data types and preferences into the system using different interfaces. Specifically, a patient-specific data entry interface 130 may be provided to permit the patient to input demographic data (e.g., age, gender, race, address, emergency contact, etc.), physical data (e.g., weight, height, blood pressure, etc.) and any other type of information deemed useful to improve the calculation of similarity metric, as will be described in greater detail later on. A patient preference adjustment interface 132 may be provided to permit the patient to enter personal preferences (e.g., distance willing to travel, etc.). The patient preference adjustment interface 132 allows patients to input their preferences using a simple interface (e.g., radio buttons for high, medium, low; checkboxes for yes, no; tuning bars for relative values; textboxes for entering numbers; etc.). The patient can specify things such as relative importance of particular outcomes, financial limits and travel-related limits, as well as hard constraints such as budgetary restrictions, location-based restrictions, confidence levels etc. For example, the patient can limit the recommendation to a particular radius relative to their home or current location, exclude certain areas (e.g., cities, zip codes, etc.) from the recommendation, exclude any number of hospitals, hospital networks or ACOs from the recommendation, etc. A patient future plan entry interface 134 may be provided to permit the patient to enter data corresponding to future plans (e.g., plans to move, retire, change insurance provider, undergo optional medical procedures, etc.). This information may be provided to the recommendation generation tool 101 to aid in making the recommendation. A subset of the information available to the hospitals/hospital networks/ACOS and insurance providers can be made available to the patient.

A non-emergency interface 136 according to the disclosure includes a terminal that helps patients interact with a recommendation display 138 and includes a substantial amount of data sufficient to permit the patient to make an informed decision, accounting for the variables described in greater detail earlier. By providing a sufficient amount of data to the patient via the display 138, the patient is able to make a well informed decision accounting for pros and cons of various alternatives in light of their past and present conditions, future plans and personal preferences. The non-emergency interface 136 may be accessible through a computer, hand-held phone, 911 operator, emergency medical technician, etc. The patient can select, evaluate and compare any of the recommendations from the display 138 as needed to obtain additional information. The non-emergency interface 136 also includes a what-if dashboard 140 that helps the patient consider various potential scenarios, either in terms of certain future events in their own lives or in terms of the choices of healthcare providers they make. Specifically, the dashboard 140 allows the patient to evaluate financial, medical and other impacts to the patient under various potential scenarios. The patient can use this information to aid in making a decision with respect to the hospital, hospital network or ACO.

The emergency interface 142 according to the disclosure includes a terminal that provides less detailed information than the non-emergency interface 136. Specifically, the emergency interface 142 may include a less descriptive and more simplified recommendation to minimize delay in receiving medical attention. The emergency interface 142 may be accessible through a computer, hand-held phone, 911 operator, emergency medical technician, etc. and includes a recommendation display 144 similar to the recommendation display 138. The recommendation display 144 may display a list of recommended hospitals, hospital networks and/or ACOs without any detailed information, the list being provided in order of closest proximity from all available hospitals, closest proximity of in-network hospitals, lowest anticipated cost, etc. In a preferred embodiment, the recommendation generation tool 100 may default to a first display order (e.g., based on proximity) in the emergency interface 142. The display order is adjustable anytime prior to or during use.

Continuing to the exemplary method, in a step 204, the recommendation generation tool 101 uses an exemplary algorithm to make a determination of one of a single and multiple optimal hospitals, hospital networks and/or ACOs based on mathematical models described in greater detail earlier. A similarity metric is used to identify similar patients and can be calculated based on a variety of criteria such as similarity in demographics, present symptoms and measurements. The similarity metric calculation process is described in greater detail below with respect to three different scenarios.

In a first exemplary scenario, a first patient $Pt_1$ with known chronic kidney problems is deemed to be "similar" to a second patient $Pt_2$ with known chronic kidney problems if:

$$S_{12}=w_1*I(\text{Gender}_1!=\text{Gender}_2)+w_2*I(\text{Race}_1!=\text{Race}_2)+w_3*|\text{Age}_1-\text{Age}_2|+w_4*|\text{Weight}_1-\text{Weight}_2|+w_5*|\text{Blood Pressure}_1-\text{Blood Pressure}_2|\leq S_{max}$$

where the subscripts 1 and 2 correspond to first and second patients $Pt_1$ and $Pt_2$ respectively. I(.) Is the indicator function that equals 1 if the expression inside the parentheses evaluates to true, and equals 0 otherwise. $w_1$ through $w_s$ are weight parameters and $S_{max}$ is the maximum distance parameter. In this case, the estimated performance x of a hospital/hospital network/ACO for a patient $Pt_1$ will be calculated as the average past performance all patients within this maximum distance $S_{max}$ from patient $Pt_1$ where $$x = \frac{\sum_{n=S_1\leq S_{max}} x_n}{n}.$$

Alternatively, the estimated performance x of a hospital, hospital network or ACO for the first patient $Pt_1$, can be calculated based on the weighted past performance of that hospital/hospital network/ACO for past patients where the weights are inversely proportional to the distance between the first patient $Pt_1$ and the past patients. This case is illustrated below:

$$x = \frac{\sum_n \frac{x_n}{S_{1n}}}{\sum_n \frac{1}{S_{1n}}}$$

In a second exemplary scenario, a similarity of a first patient $Pt_1$ known to have diabetes to a second patient $Pt_2$ also known to have diabetes is based on:

$$S_{12}=w_1*|\text{BMI}_1-\text{BMI}_2|+w_2*|\text{Blood Pressure}_1-\text{Blood Pressure}_2|+w_3*I(\text{HeartDisease}_1!=\text{HeartDisease}_2)+w_4*I(\text{Symptoms}_1!=\text{Symptoms}_2)+w_4*I(\text{FamilyHistoryOfDiabetes}_1!=\text{FamilyHistoryOfDiabetes}_2)$$

where the subscripts 1 and 2 correspond to first and second patients $Pt_1$ and $Pt_2$ respectively. I(.) Is the indicator function that equals 1 if the expression inside the parentheses evaluates to true, and equals 0 otherwise. $w_1$ through $w_s$ are weight parameters.

In a third exemplary scenario, a medical condition of the first patient $Pt_1$ is not known. Whereas the first and second scenarios used a current medical condition (i.e., kidney problems, diabetes) to determine similarity to another patient, the second scenario addresses a situation where the medical condition is not known or is currently undiagnosed. In this case, the similarity measure relies on the patient basic demographic information, past history, as well as symptoms, according to the following algorithm:

$$S_{12}=w_1*I(Gender_1!=Gender_2)+w_2*|Age_1-Age_2|+ \\ W_3*|BMI_1-BMI_2|+W_4*I \\ (FamilyMedHistory_1!=FamilyMedHistory_2)+ \\ W_5*I(Symptoms_1!=Symptoms_2)$$

where the subscripts 1 and 2 correspond to first and second patients $Pt_1$ and $Pt_2$ respectively. I(.) Is the indicator function that equals 1 if the expression inside the parentheses evaluates to true, and equals 0 otherwise. $w_1$ through $w_s$ are weight parameters.

Once a similar patient or patients have been identified, the recommendation generation tool 101 uses the previous patient data to help make a recommendation to the current patient. Once the recommendation of step 204 is made, the recommendation generation tool 101 determines, in step 206, if emergency or non-emergency mode is being used. If an emergency mode is being used, the method proceeds to step 208 wherein a simplified emergency interface is displayed to the user. If a non-emergency mode is being used, the method proceeds to step 210 wherein a detailed non-emergency interface is displayed to the user.

Figure 3:
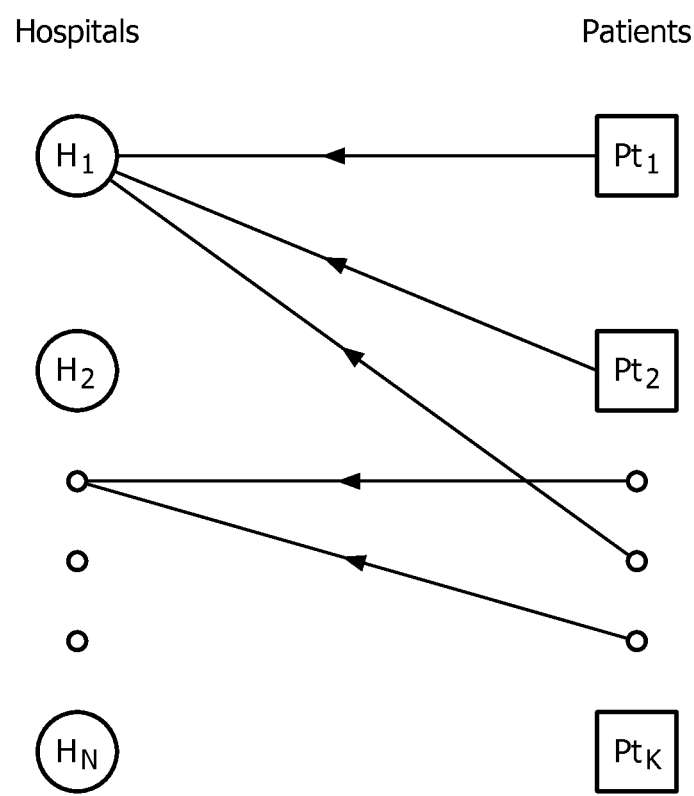
FIG. 3 depicts a recommendation allocation chart according to an exemplary embodiment.

FIG. 3 depicts a schematic view of a simultaneous association of patients to hospitals within a hospital network or ACO. Specifically, it is evident from FIG. 2 that the first patient $Pt_1$, second patient $Pt_2$ and any number of additional patients extending to $Pt_K$ can be associated with any of the first hospital $H_1$, second hospital $H_2$ and any number of additional hospitals extending to $H_N$. FIG. 3 depicts how a bipartite-graph based matching problem can be solved to find the best possible simultaneous association of patients to hospitals while respecting the vacancies available and accounting for specific hospitals expertise. Once the association between hospitals and patients has been ascertained from the hospital network/ACOs perspective, then the next step will be providing the incentives to patients to attract them to specific hospitals within the network.

This recommendation generation tool 101 may be used as a tool for hospital networks and ACOs to attract patients through the right set of incentives, for insurance providers to direct patients to the appropriate medical facilities through customized recommendations and incentives and as a stand-alone tool for patients to aid in selection of a hospital, hospital network or ACO.

Those skilled in the art will understand that the above-described exemplary embodiments may be implemented in any number of manners, including, as a separate software module, as a combination of hardware and software, etc. For example, the recommendation generation tool 101 may be a program containing lines of code that, when compiled, may be executed on a processor. The programs may be embodied on a non-transitory computer readable storage medium.

It is noted that the claims may include reference signs/numerals in accordance with PCT Rule 6.2(b). However, the present claims should not be considered to be limited to the exemplary embodiments corresponding to the reference signs/numerals.

It will be appreciated by those skilled in the art that various modifications and alterations of the invention can be made without departing from the broad scope of the appended claims. Some of these have been discussed above and others will be apparent to those skilled in the art.

The invention claimed is:

1. A method, comprising:
receiving medical data, geographical data and financial data corresponding to a patient;
comparing the medical data, the geographical data and the financial data to corresponding data of a plurality of medical provider databases to determine a relationship therebetween,
wherein at least one medical provider database is connected to a corresponding incentive generation process;
displaying at least one incentive for selecting a particular medical provider, the incentive including one or both of a financial and priority-based incentive;
executing an algorithm to determine a degree of similarity between the patient and previous patients served by each of the plurality of medical providers, wherein the algorithm comprises inputs related to patient demographics and symptoms, and the previous patients are similar to the patient when the degree of similarity is within a predetermined threshold; and
generating, via a recommendation generation tool, a recommendation of a first medical provider for the patient based on parameters including the medical data, the geographical data, the financial data, the comparison to the corresponding data of the medical provider databases, the available incentives for selecting a particular medical provider, an outcome-based performance of the medical providers across similar previous patients, and one of an emergency situation or a non-emergency situation wherein a first interface is displayed for an emergency mode and a second interface is displayed for a non-emergency mode, wherein the second interface includes data in the recommendation that is not included in the first interface, the data comprising past and present conditions and future plans of a user.

2. The method of claim 1, wherein each of the plurality of medical providers is a hospital.

3. The method of claim 1, wherein each of the plurality of medical providers is a hospital network further comprising one or more hospitals associated therewith, the method further comprising the step of generation of a recommendation of a hospital within the hospital network.

4. The method of claim 1, wherein each of the plurality of medical providers is an Accountable Care Organization (ACO) further comprising one or more hospitals associated therewith, the method further comprising the step of generation of a recommendation of a hospital within the ACO.

5. The method of claim 1, wherein the incentive generation process is based on a vacancy of hospital beds with the predetermined medical provider.

6. The method of claim 1, further comprising the step of receiving, via a patient data entry interface, data corresponding to one or more of medical, demographic, geographical and financial data of the patient and using this data to make the recommendation.

7. The method of claim 1, further comprising the step of receiving, via a patient future plan entry interface, data corresponding to one or more of future medical, future financial and future geographical plans of the patient and using this data to make the recommendation.

8. The method of claim 1, wherein the medical provider database includes all information proprietary to the medical provider on demographic, medical, claims-related, and financial aspects of all the individuals served in the past and present by the insurance provider as well as all the information publicly reported by an insurance provider.

9. The method of claim 1, wherein the medical provider database includes all information proprietary to the medical provider on procedural, diagnostic, outcomes-related and financial aspects of all the patients served in the past and present by the medical provider as well as information publicly reported by the medical provider.

10. The method of claim 1, wherein the recommendation generation results in two or more pareto-optimal recommendations.

11. The method of claim 1, wherein the recommendation is for emergency situations, the recommendation generation tool including a terminal accessible to the patient through one or more of a computer, smart-phone and a 911 call-center.

12. The method of claim 1, wherein the recommendation is for non-emergency situations.

13. The method of claim 1, wherein the geographical data is more heavily weighted in generating the recommendation during the emergency situation than during the non-emergency situation.

14. A system for selecting a medical provider from a plurality of available medical providers, comprising:
a memory storing a plurality of medical provider databases associated with each of a plurality of medical providers, the medical provider databases including data corresponding to demographic, medical, geographic, claims-related and financial aspects of patients served in the past by each respective medical provider and a set of instructions,
wherein at least one medical provider database is connected to a corresponding incentive generation process, the incentive generation process displaying at least one available incentive for selecting a particular medical provider, the incentive including one or both of a financial and priority-based incentive; and
a processor that executes the instructions to perform operations, comprising executing an algorithm to determine a degree of similarity between the patient and previous patients served by each of the plurality of medical providers, wherein the algorithm comprises inputs related to patient demographics and symptoms, and the previous patients are similar to the patient when the degree of similarity is within a predetermined threshold, determining a medical provider suited to patient data including_medical, geographical and financial needs of a patient, the determination being made based on a comparison of the patient data with the one or more medical provider databases, the at least one available incentive for selecting a particular medical provider, and an outcome-based performance of the medical providers across similar previous patients, generating a recommendation based on the comparison and one of an emergency situation or a non-emergency situation, and generating a display for the recommendation on a display to the patient wherein a first interface is displayed for an emergency mode and a second interface is displayed for a non-emergency mode, wherein the second interface includes data in the recommendation that is not included in the first interface, the data comprising past and present conditions and future plans of a user.

15. The system of claim 14, wherein the processor is adapted to compare the patient data with past patient data of a subset of patients having similar medical diagnoses.

16. The system of claim 14, wherein the processor is adapted to make the recommendation based on future patient data corresponding to one or more of future medical data, future financial data and future geographical data.

17. The system of claim 14, wherein the medical provider is one of a hospital, hospital network and ACO.

18. The system of claim 17, wherein if the medical provider is a hospital network or ACO, the process generates a further recommendation corresponding to a particular hospital associated with the hospital or ACO.

19. A non-transitory computer-readable storage medium with an executable program stored thereon, wherein the program instructs a processor to perform the following operations:
receiving medical data, geographical data and financial data corresponding to a patient;
comparing the medical data, the geographical data and the financial data to corresponding data of a plurality of medical provider databases to determine a relationship therebetween,
wherein at least one medical provider database is connected to a corresponding incentive generation process;
displaying at least one available incentive for selecting a particular medical provider, the incentive including one or both of a financial and priority-based incentive;
executing an algorithm to determine a degree of similarity between the patient and previous patients served by each of the plurality of medical providers, wherein the algorithm comprises inputs related to patient demographics and symptoms, and the previous patients are similar to the patient when the degree of similarity is within a predetermined threshold; and
generating, via a recommendation generator, a recommendation of a first medical provider for the patient based on parameters including the medical data, the geographical data, the financial data, the comparison to the corresponding data of the medical provider databases, the available incentives for selecting a particular medical provider, an outcome-based performance of the medical providers across similar previous patients, and one of an emergency situation or a non-emergency situation wherein a first interface is displayed for an emergency mode and a second interface is displayed for a non-emergency mode, wherein the second interface includes data in the recommendation that is not included in the first interface, the data comprising past and present conditions, and future plans of a user.

* * * * *